United States Patent [19]

Dearnaley et al.

[11] Patent Number: 5,725,573
[45] Date of Patent: *Mar. 10, 1998

[54] MEDICAL IMPLANTS MADE OF METAL ALLOYS BEARING COHESIVE DIAMOND LIKE CARBON COATINGS

[75] Inventors: Geoffrey Dearnaley; James Lankford, Jr., both of San Antonio, Tex.

[73] Assignee: Southwest Research Institute, San Antonio, Tex.

[*] Notice: The term of this patent shall not extend beyond the expiration date of Pat. Nos. 5,391,407 and 5,605,714.

[21] Appl. No.: 630,141

[22] Filed: Apr. 10, 1996

Related U.S. Application Data

[63] Continuation-in-part of Ser. No. 472,495, Jun. 7, 1995, Pat. No. 5,605,714, which is a continuation-in-part of Ser. No. 220,234, Mar. 29, 1994, Pat. No. 5,593,719.

[51] Int. Cl.$^6$ .............................. A61F 2/24; C23C 14/00; B05D 3/00; B32B 9/00
[52] U.S. Cl. .................... 623/2; 427/2.25; 427/2.24; 427/525; 427/530; 427/528; 427/527; 427/534; 428/698; 428/448; 428/450; 423/446; 623/11
[58] Field of Search ............................... 427/2.24, 2.26, 427/2.25, 527, 528, 530, 525, 534; 423/446; 623/2, 12, 11, 18, 19, 20, 21, 22, 23; 428/448, 450, 698

[56] References Cited

U.S. PATENT DOCUMENTS

| | | |
|---|---|---|
| 3,662,440 | 5/1972 | Snedeker et al. |
| 3,707,006 | 12/1972 | Bokoros et al. |
| 3,717,522 | 2/1973 | Shirato et al. |
| 4,362,681 | 12/1982 | Spector et al. |
| 4,410,611 | 10/1983 | MacIver |
| 4,452,827 | 6/1984 | Kolev et al. |
| 4,465,715 | 8/1984 | Manabe et al. |
| 4,486,286 | 12/1984 | Lewin et al. |
| 4,495,044 | 1/1985 | Banks |
| 4,554,208 | 11/1985 | MacIver et al. |
| 4,647,494 | 3/1987 | Meyerson et al. |
| 4,698,236 | 10/1987 | Kellogg et al. |
| 4,725,345 | 2/1988 | Sakamoto et al. |
| 4,743,493 | 5/1988 | Sioshansi et al. |
| 4,746,538 | 5/1988 | Mackowski |
| 4,756,964 | 7/1988 | Kincaid et al. |
| 4,770,902 | 9/1988 | Barlow et al. |
| 4,772,513 | 9/1988 | Sakamoto et al. |
| 4,778,469 | 10/1988 | Lin et al. |
| 4,822,355 | 4/1989 | Bhuvaneshwar |
| 4,822,466 | 4/1989 | Rabalais et al. |
| 4,842,937 | 6/1989 | Meyer et al. |
| 4,877,677 | 10/1989 | Hirochi et al. |
| 4,961,958 | 10/1990 | Desphandey et al. |
| 4,966,803 | 10/1990 | Pluyter et al. |
| 4,981,071 | 1/1991 | Enke |
| 4,988,421 | 1/1991 | Drawl et al. |
| 4,992,153 | 2/1991 | Bergmann et al. |
| 4,992,298 | 2/1991 | Deutchman et al. |
| 5,009,923 | 4/1991 | Ogata et al. |
| 5,028,451 | 7/1991 | Ito et al. |
| 5,064,682 | 11/1991 | Kiyama et al. |
| 5,084,151 | 1/1992 | Vallana et al. |
| 5,130,161 | 7/1992 | Mansur et al. |
| 5,133,757 | 7/1992 | Sioshansi et al. |
| 5,133,845 | 7/1992 | Vallana et al. |
| 5,135,808 | 8/1992 | Kimock et al. |
| 5,169,597 | 12/1992 | Davidson et al. |
| 5,176,710 | 1/1993 | Hahn et al. |
| 5,192,330 | 3/1993 | Chang et al. |
| 5,192,523 | 3/1993 | Wu et al. |
| 5,219,363 | 6/1993 | Crowninshield et al. |
| 5,223,045 | 6/1993 | Priceman |
| 5,228,451 | 7/1993 | Bales et al. |
| 5,232,568 | 8/1993 | Parent et al. |
| 5,246,884 | 9/1993 | Jaso et al. |
| 5,249,554 | 10/1993 | Tamor et al. |
| 5,252,174 | 10/1993 | Deguchi et al. |
| 5,270,252 | 12/1993 | Papanicolaou |
| 5,314,492 | 5/1994 | Hamilton et al. |
| 5,391,407 | 2/1995 | Dearnaley |
| 5,415,704 | 5/1995 | Davidson |
| 5,425,777 | 6/1995 | Sarkisian et al. |
| 5,645,900 | 7/1997 | Ong et al. |

FOREIGN PATENT DOCUMENTS

| | | |
|---|---|---|
| 0 548 788 | 6/1993 | European Pat. Off. |
| 0 548 799 A1 | 6/1993 | European Pat. Off. |
| 62-196371 | 8/1987 | Japan |
| 62-202897 | 9/1987 | Japan |
| 1147067-A | 6/1989 | Japan |

OTHER PUBLICATIONS

J. Lankford, et al., "Adherence of Diamondlike Carbon Coatings on total Joint Substrate Materials," *Nuclear Instruments and Methods in Physics Research B80/81*, Part II, 1993, 1441–1445.

John H. Dumbleton, Ph.K., "The Clinical Significance of Wear in Total Hip and Knee Prostheses," *Journal of Biomaterials Applications*, 3, Jul. 1988, 3, 10–32.

G. Dearnaley, et al., "Bioapplications of Diamond–like Carbon Coatings," 4th World Biomaterials Congress, Berlin, Apr. 1992.

A.M. Jones, et al., "Stress and Microstructure of Diamond–like Carbon from Ion–beam Decomposition of Hydrocarbon Precursors," 2nd European Conference on Diamond, Diamond–like and Related Coatings, Nice, France, Sep. 2–6, 1991.

C.J. Bedell, et al., "Diamond–like Carbon from the Ion–beam Decomposition of Polyphenyl Ether," *Applications of Diamond Films & Related Materials*, 1991, 833–838. No month.

(List continued on next page.)

*Primary Examiner*—Marianne Padgett
*Attorney, Agent, or Firm*—Madan & Morris, PLLC

[57] ABSTRACT

The present invention provides a method for coating a metal alloy component of a medical implant, particularly a component of a heart valve made of a titanium base alloy, with a strongly adhered coating of diamond-like carbon. The method uses ion beam assisted deposition to form a gradient at the surface of the titanium alloy comprising metal alloy/metal-silicide/(silicon or germanium)/silicon- or germanium-carbide/DLC.

36 Claims, No Drawings

OTHER PUBLICATIONS

J.A. Davidson, Ph.D., et al., "Surface Modification Issues for Orthopaedic Implant Bearing Surfaces," *Surface Modification Technologies V*, 1992, 1–14. No month.

P. Bodo, et al., "Adhesion of Evaporated Titanium to Polyethylene: Effects of Ion Bombardment Pretreatment," *J. Vac. Sci A 2*, 4, Oct.–Dec. 1994, 1498–1502.

P. Gao, et al., "Surface Treatment of Ultra High Molecular Weight Polyethylene to Enhance adhesion and Conductivity Properties" presented at Physical Aspects of Polymer Science, Sep., 9–11, 1991, Univ. of Leeks, UK. No month.

A.C. Evans, et al., "Diamond–like Carbon Applied to Bioengineering Materials," *Medical Device Technology*, May 1991, 26–29.

C.M. Agralwal, et al., "The Effects of Diamond–Like–Carbon Coatings on the Friction and Wear of Enhanced UHMWPE–Metal Couples," 19th Annual Meeting of Society for Biomaterials, Apr. 28–May 2, 1993.

L.S. Wielunski, et al., "Improvement of Thermally Formed Nickel Silicide by Ion Irradiation," *J. Vac. Sci. Technol.*, 20(2), Feb. 1982, 182–184.

R.S. Butter, et al., "Diamond–Like Carbon for Biomedical Applications," Applied Diamond Conference, Aug. 21–24, 683, 688 and 690.

Keith O. Legg, "Surface Engineering with Ion–Assisted Coatings," Nuclear Instruments and Methods in Physics Research B24/25 (1987), pp. 565–567. No month.

G. Dearnaley, "Materials Science Aspects of Ion Beam Technology," Surface Engineering, vol 7, No. 2 (1991), pp. 127–136. No month.

San Antonio Express–News Science Article, "Diamond Coating may be future of tool manufacture" (Apr. 1, 1996).

5,725,573

MEDICAL IMPLANTS MADE OF METAL ALLOYS BEARING COHESIVE DIAMOND LIKE CARBON COATINGS

The present application is a continuation-in-part of application Ser. No. 08/472,495, filed Jun. 7, 1995, now U.S. Pat. No. 5,605,714 which is a continuation-in-part of application Ser. No. 08/220,234, filed Mar. 29, 1994, now U.S. Pat. No. 5,593,719.

FIELD OF THE INVENTION

The present invention relates to cohesively adhering a diamond-like carbon coating to a medical implant made of a metal alloy. More particularly, the present invention relates to cohesively adhering a diamond-like carbon coating to a heart valve made of a titanium base alloy.

BACKGROUND OF THE INVENTION

Titanium has become a popular metal for the manufacture of human implants. The FDA considers titanium and many of its alloys to be biocompatible. Titanium base materials also are easily machined, are not overly brittle, and are durable enough for the manufacture of most medical implants.

Unfortunately, titanium base materials also tend to encourage thrombogenesis. This tendency is undesirable, particularly for implants used in the circulatory system. An example of a medical implant that is used in the circulatory system is a heart valve.

A method for reducing the thrombogeneticity of titanium and its alloys would be highly desirable.

SUMMARY OF THE INVENTION

The present invention provides a method for strongly adhering a diamond-like carbon coating to a medical implant comprising a metal alloy. In a preferred embodiment, the metal alloy is a titanium base alloy and the DLC coating reduces the thrombogeneticity of the component. The method comprises: exposing the metal alloy substrate to a vacuum; heating the substrate; depositing silicon or germanium onto the substrate while substantially simultaneously bombarding the substrate with a first energetic beam of ions to form an intermetallic bonding layer cohesively bonded to an interlayer of silicon or germanium; condensing a film of diamond-like carbon precursor onto the interlayer of silicon or germanium and substantially simultaneously bombarding the substrate with a second energetic beam of ions to form a silicon or germanium carbide bonding layer cohesively bonded to a coating of diamond-like carbon. The resulting component has the following gradient at its surface: metal alloy/metal-silicide/(silicon or germanium)/silicon- or germanium-carbide/DLC.

DETAILED DESCRIPTION OF THE INVENTION

Amorphous carbon, or "diamond-like carbon" ("DLC"), is a biocompatible coating material that is less thrombogenic than titanium. A primary concern about using DLC for medical implants is the strength of the bond that forms between the substrate and the DLC coating. The present invention provides a method for forming a tightly adhered coating of DLC on metal alloy components for use in the circulatory system, preferably components made of a titanium-base alloy. The DLC coating reduces friction and wear in components made of substantially any metal alloy. Where the metal alloy is a titanium-base alloy, the DLC coating also reduces the thrombogeneticity of the component.

The present invention would work with pure metals as well as metal alloys; however, as a practical matter, a metal must be alloyed in order to form a viable industrial component. The present invention may be used to form a DLC coating on a component made of substantially any metal alloy. Preferred metal alloys should form a strongly-cohesive silicide and/or germanide—that is, an intermetallic compound in which the bonding is partially metallic and partially covalent. Metal substrates that form strongly-cohesive silicides and/or germanides include cobalt, nickel, titanium, zirconium, chromium, molybdenum, tungsten, platinum, and palladium. Titanium, cobalt, and stainless-steel are metals that have been approved by the FDA for use in medical implants. For this reason, titanium, cobalt, and stainless-steel are preferred metals for the components of the present invention. Components made of a titanium-base alloy are most preferred because titanium has less thrombogeneticity than other metals.

The present method for treating the metal alloy component to provide a diamond-like carbon (DLC) coating uses ion beam assisted deposition of silicon, germanium, or a combination thereof, followed by ion beam assisted deposition of DLC. Although a combination of silicon and germanium can be used to form the interlayer, it is preferred to use silicon or germanium, alone, because of the difference between the vaporization points of the two materials. DLC is known to adhere better to silicon than to any other substrate—which is attributed to strong SiC bonds formed at the interface of the two materials. Titanium also is known to react with silicon to form a disilicide ($TiS_2$) when reacted with silicon. Germanium is similar to silicon and produces similar results.

In order to effectively knit together the successive layers of metal-silicon-DLC (or metal-germanium-DLC), it is necessary to supply a bond-interface (a) between the metal and the silicon or germanium, as well as (b) between the silicon or germanium and the DLC. Without limiting the present invention, the invention is believed to achieve this result by forming a gradient in the type of bonds found in progressive layers of material at the surface of the metal alloy. In essence, the gradient is believed to be: intermetallic bonds in the metal alloy substrate; partially metallic and partially covalent bonds between the metal and silicon or germanium in a layer of metal silicide; primarily covalent but somewhat metallic bonds in a layer of silicon or germanium, which strongly coheres to the layer of metal silicide; covalent bonds between the silicon or germanium and carbon atoms in the DLC in a layer of silicon- or germanium carbide; and, covalent bonds in the layer of DLC, which strongly coheres to the layer of silicon or germanium-carbide.

In order to form the gradient of the present invention, the metal alloy component should be cleaned using conventional methods to remove superficial contaminants, such as grease. The clean component should be placed in a vacuum chamber that has been evacuated to a base pressure of preferably less than about $10^{-5}$ torr. The component then should be bombarded with ions, preferably argon ions, at an energy range between about 10–100 keV, preferably around 10 keV. This ion bombardment provides an effective means to remove some of the remaining adsorbed atoms from the surface.

The component then is heated. If the component is a titanium base component, then the component will tend to have a thin oxide layer on its surface which should be removed in order to form the silicide/germanide layer. This is accomplished by heating the titanium component sufficiently to "dissolve" the oxide layer, or to cause the oxygen in the layer to diffuse inward from the surface to the interior. The component preferably should be heated to about 600°–650° C. (1112°–1202° F.) before condensing silicon and/or germanium onto the surface of the component.

After the component has been heated and while remaining at 600°–650° C. (1112°–1202° F.), silicon and/or germanium can be deposited onto the surface of the component using known means. A preferred means is to position the workpiece directly over a volatilization hearth which is maintained at the vaporization temperature of the silicon or germanium until a preferred coating thickness of between about 100–200 nm has been achieved. The thickness of the coating may be monitored by standard methods, e.g., using the frequency change of a quartz crystal oscillator that is exposed to the flux of coating atoms during deposition.

The component preferably should be simultaneously bombarded with an energetic beam of ions, preferably nitrogen ions, at an energy range between about 500 eV to 100 keV, preferably between about 10–20 keV, in order to form a layer of metal-silicide/metal-germanide at the metal-silicon/germanium interface. Nitrogen is preferred for the ion beams of the present invention because nitrogen ions actually will bond with the substrate/coating or interlayer. Inert ions, such as argon and/or helium ions, will not bond with the substrate/film. The use of inert ions could result in bubbling and/or a weaker coating. Although it has not been proven, it is believed that strong carbon-nitrogen bonds form in the DLC layer when the ions used to make the DLC are nitrogen ions. In any event, the use of a beam of nitrogen ions can result in DLC coatings that increase wear resistance and decrease friction up to 5–7 times more than DLC coatings formed using other types of ions.

Although nitrogen ions are preferred, other ions may be used, such as argon, hydrogen, silicon, methane, helium, or neon, having an energy between 500 eV to 100 keV, preferably 10–20 keV. The "ion arrival ratio"—defined as the ratio of each arriving ion to the number of atoms of silicon, germanium, or DLC precursor present at the surface of the component—preferably should be at least 1:10.

Thereafter, the component should be cooled to at least below about 100° C. (212° F.), preferably to about 80° C. (176° F). The cooling preferably should be done without removing the component from the vacuum chamber. Thereafter, a diamond-like carbon (DLC) precursor should be deposited. In a preferred embodiment, the DLC precursor is polyphenyl ether. Other suitable precursor materials include carbon-based diffusion pump materials which have a low vapor pressure and can be vaporized stably at room temperature. Preferable diffusion pump fluids include, but are not necessarily limited to: polyphenyl ether; polydimethyl siloxane; pentaphenyltrimethyl siloxane; and, elcosyl napthalene.

The precursor is vaporized and condensed onto the surface of the component using known means. Generally, the precursor is placed in a reservoir, heated to between about 150° C.–170° C. (302° F.–338° F.), and directed onto the cooled component. Substantially simultaneously, the component should be bombarded, either in a continuous or interrupted fashion, with an energetic beam of ions. A preferred ion source is nitrogen. Other suitable ions include, but are not necessarily limited to, argon, hydrogen, silicon, methane, helium, or neon. The ion beam should have an energy between about 500 eV to 100 keV, preferably between about 10–30 keV. The energy of bombardment must be sufficient to ionize the constituent molecules in the precursor film, and to rupture the bonds between hydrogen and other atoms, thereby releasing the hydrogen into the surrounding vacuum to be pumped away.

The rate of arrival of the ions, related to the "ion arrival ratio," should be controlled in relation to the rate of arrival of the precursor molecules. This process should require about one ion for every 100 atoms in the final product coating; however, the required ion-to-atom ratio will vary according to the mass and energy of the ion species. Typically, 100 eV must be deposited for each carbon atom in the coating. The function of this second ion bombardment step is to rupture at least about 80% of the carbon-hydrogen bonds an the precursor, resulting in the formation of a noncrystalline coating of amorphous carbon. The energy dissipated by the energetic ion bombardment during ion beam assisted deposition is in the form of inelastic electronic excitations equivalent to at least about 100 eV for each carbon atom within the deposited coating. This energy dissipation strongly enhances adhesion of the DLC coating by rupturing and subsequently reforming interatomic bonds across the interfaces. Persons of ordinary skill in the art will recognize how to achieve the correct linear energy of transfer in the ionizing process. The procedure should be continued until a thickness of DLC between about 100 nm–10 microns is achieved.

EXAMPLE 1

A DLC coating of approximately 1 micron in thickness is prepared by nitrogen ion bombardment of a polyphenyl ether precursor. A titanium base heart valve comprised of a titanium alloy containing vanadium and aluminum is cleaned in isopropyl alcohol prior to coating. Isopropyl alcohol is chosen because it leaves few, if any, residues. Wear testing reveals that, under some circumstances, there could be a loss of adhesion of the coating.

EXAMPLE 2

A titanium alloy heart valve of the same composition as in Example 1 is treated using a bond-coat of silicon. After conventional solvent cleaning of the component to remove superficial contaminants, such as grease, the component is placed in a vacuum chamber that has been evacuated to a base pressure of $10°$ torr. The component then is bombarded with nitrogen ions at an energy of about 10 keV to remove some of the remaining adsorbed atoms from the surface.

The component is heated to about 600° C. (1112° F.). Silicon then is deposited onto the outer surface of the component. The workpiece is positioned directly over the volatilization hearth which is maintained at a temperature of about 1900° C. (3450° F.), until a preferred coating thickness of about 100 nm has been achieved. The thickness of the coating is monitored by standard methods, e.g., using the frequency change of a quartz crystal oscillator that is exposed to the flux of coating atoms during deposition.

The component is simultaneously bombarded with an energetic beam of nitrogen ions at an energy of about 20 keV and an ion-to-atom ratio of at least 1 ion to 10 silicon atoms for about 15 minutes to form a layer of metal silicide at the metal-silicon interface.

Thereafter, the component is cooled to about 80° C. without removing the component from the vacuum chamber. Polyphenyl ether is heated to at least about 150° C. (302° F.) and condensed onto the surface of the component. The component simultaneously is bombarded with an energetic beam of nitrogen ions having an energy of about 20 keV and an ion-to-atom ratio of at least 1 ion to 100 precursor molecules. The procedure is continued until a thickness of DLC of about 100 nm is achieved.

In prolonged wear tests, at a contact pressure of 6.9 MPa under serum, i.e., load and environmental conditions equivalent to those encountered in vivo by a heart valve, no decohesion or loss of DLC is observed after about 10.0 million reciprocated wear cycles.

EXAMPLE 3

A titanium alloy heart valve of the same composition as in Example 1 is treated using a bond-coat of germanium. After conventional cleaning of the valve to remove superficial contaminants, the valve is placed in a vacuum chamber that has been evacuated to a base pressure of $10^{-5}$ torr. The valve then is cleaned by bombardment with argon ions at an energy of 10 keV. The component is heated to about 600° C. (1112° F.). Germanium then is deposited onto the outer surface of the component. The workpiece is positioned directly over the volatilization hearth which is maintained at a temperature of about 450° C. (232° F.) until a coating of germanium having thickness of about 100 nm is achieved. The thickness of the coating is monitored using the frequency change of a quartz crystal oscillator. The valves are substantially simultaneously bombarded with an energetic beam of nitrogen ions at about 15 keV and at an ion arrival ratio of at least 1:10. Thereafter, the valves are cooled in the vacuum chamber to about 80° C. (26° F.).

Polyphenyl ether is placed in a reservoir, heated to about 150° C. (302° F.), and the resulting vapor is directed onto the cooled valves. Substantially simultaneously, the component is bombarded with an energetic beam of nitrogen ions at an energy of about 20 keV and an ion arrival ratio of about 1:100 atoms in the final product coating, or at about 100 eV for each carbon atom in the coating. The procedure is continued until a thickness of DLC of about 100 nm is achieved. Subsequent wear testing demonstrates enhanced wear resistance.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A method for coating a metal alloy component of a medical implant with diamond-like carbon comprising:

exposing said component to a vacuum at a pressure of about $10^{-5}$ torr or less;

heating said component to a first temperature of about 300° C. (149° F.) or, if said metal alloy is temperature sensitive, to a highest temperature acceptable for said metal alloy;

depositing onto said component an intermediate material selected from the group consisting of silicon, germanium, and a combination thereof, in an amount sufficient to form an intermetallic material selected from the group consisting of a metal-silicide, a metal-germanide, and a combination thereof at said outer surface of said substrate cohesively bonded to an interlayer of said intermediate material;

substantially simultaneous with said depositing of said intermediate material, bombarding said intermediate material with a first energetic beam of ions at a first energy, a first ion arrival ratio, and for a first amount of time sufficient to form said intermetallic bonding layer cohesively bonded to said interlayer;

condensing a diamond-like carbon precursor onto said interlayer at a second temperature and for a second amount of time sufficient to form a film of precursor molecules on said interlayer, wherein said second temperature is sufficiently low that said diamond-like carbon precursor is not vaporized off of said substrate;

substantially simultaneous with said condensing of said diamond-like carbon precursor, bombarding said diamond-like carbon precursor with a second energetic beam of ions at a second energy, a second ion arrival ratio, and for a third amount of time sufficient to form a carbide bonding layer selected from the group consisting of silicon-carbide, germanium-carbide, and a combination thereof, cohesively bonded to a coating of diamond-like carbon.

2. The method of claim 1 wherein said metal alloy comprises a metal selected from the group consisting of cobalt, nickel, titanium, zirconium, chromium, molybdenum, tungsten, platinum, palladium, and combinations thereof.

3. The method of claim 1 wherein said component comprises a metal alloy selected from the group consisting of stainless steel, a cobalt base alloy, and a titanium base alloy.

4. The method of claim 3 wherein said second beam of ions comprises nitrogen ions.

5. The method of claim 4 wherein said first energy and said second energy are between about 10–30 keV.

6. The method of claim 3 wherein said second temperature is about 80° C. (26° F.).

7. The method of claim 5 wherein said second temperature is about 80° C. (26° F.).

8. The method of claim 7 wherein said intermediate material is deposited onto said substrate to a thickness of between about 100–200 nm.

9. A method for coating a titanium base component of a medical implant with diamond-like carbon comprising:

exposing said component to a vacuum at a pressure of about $10^{-5}$ torr or less;

heating said component to at least about 600° C.–650° C. (1112°–1202° F.);

depositing onto said component an intermediate material selected from the group consisting of silicon, germanium, and a combination thereof, in an amount sufficient to form an intermetallic material selected from the group consisting of titanium-silicide, titanium-germanide, and a combination thereof at said outer surface of said substrate cohesively bonded to an interlayer of said intermediate material;

substantially simultaneous with said depositing of said intermediate material, bombarding said intermediate material with a first energetic beam of ions at a first energy, a first ion arrival ratio, and for a first amount of time sufficient to form said intermetallic bonding layer cohesively bonded to said interlayer;

condensing a diamond-like carbon precursor onto said interlayer at a second temperature and for a second amount of time sufficient to form a film of precursor molecules on said interlayer, wherein said second temperature is sufficiently low that said diamond-like carbon precursor is not vaporized off of said substrate;

substantially simultaneous with said condensing of said diamond-like carbon precursor, bombarding said diamond-like carbon precursor with a second energetic beam of ions at a second energy, a second ion arrival ratio, and for a third amount of time sufficient to form a carbide bonding layer selected from the group consisting of silicon-carbide, germanium-carbide, and a combination thereof, cohesively bonded to a coating of diamond-like carbon.

10. The method of claim 9 wherein said second beam of ions comprises nitrogen ions.

11. The method of claim 9 wherein said first energy and said second energy are between about 10–30 keV.

12. The method of claim 10 wherein said first energy and said second energy are between about 10–30 keV.

13. The method of claim 9 wherein said second temperature is about 80° C. (26° F.).

14. The method of claim 10 wherein said second temperature is about 80° C. (26° F.).

15. The method of claim 12 wherein said second temperature is about 80° C. (26° F.).

16. The method of claim 9 wherein said intermediate material is deposited onto said substrate to a thickness of between about 100–200 nm.

17. The method of claim 10 wherein said intermediate material is deposited onto said substrate to a thickness of between about 100–200 nm.

18. The method of claim 12 wherein said intermediate material is deposited onto said substrate to a thickness of between about 100–200 nm.

19. The method of claim 15 wherein said intermediate material is deposited onto said substrate to a thickness of between about 100–200 nm.

20. A titanium base component of a medical implant comprising a coating of diamond-like carbon produced by a process comprising:

exposing said component to a vacuum at a pressure of about $10^{-5}$ torr or less;

heating said component to at least about 600° C.–650° C. (1112°–1202° F.);

depositing onto said component an intermediate material selected from the group consisting of silicon, germanium, and a combination thereof, in an amount sufficient to form an intermetallic material selected from the group consisting of titanium-silicide, titanium-germanide, and a combination thereof at said outer surface of said substrate cohesively bonded to an interlayer of said intermediate material;

substantially simultaneous with said depositing of said intermediate material, bombarding said intermediate material with a first energetic beam of ions at a first energy, a first ion arrival ratio, and for a first amount of time sufficient to form said intermetallic bonding layer cohesively bonded to said interlayer;

condensing a diamond-like carbon precursor onto said interlayer at a second temperature and for a second amount of time sufficient to form a film of precursor molecules on said interlayer, wherein said second temperature is sufficiently low that said diamond-like carbon precursor is not vaporized off of said substrate;

substantially simultaneous with said depositing of said intermediate material, bombarding said diamond-like carbon precursor with a second energetic beam of ions at a second energy, a second ion arrival ratio, and for a third amount of time sufficient to form a carbide bonding layer selected from the group consisting of silicon-carbide, germanium-carbide, and a combination thereof, cohesively bonded to a coating of diamond-like carbon.

21. A titanium base component of a medical implant having an outer surface comprising a sequential gradient as follows:

an intermediate material selected from the group consisting of silicon, germanium, and a combination thereof, chemically bonded to said titanium in said substrate forming an intermetallic material selected from the group consisting of titanium silicide, titanium germanide, and a combination thereof;

an interlayer material comprising said intermediate material cohesively bonded to said intermetallic material;

carbon chemically bonded to said interlayer material, forming a carbide selected from the group consisting of silicon carbide, germanium carbide, and a combination thereof; and a diamond-like carbon coating cohesively bonded to said carbide.

22. The component of claim 21 wherein said medical implant is a heart valve.

23. The component of claim 21 further comprising nitrogen bonded to carbon atoms in said diamond-like carbon.

24. The component of claim 22 further comprising nitrogen bonded to carbon atoms in said diamond-like carbon.

25. A solid metal alloy component having an outer surface comprising a sequential gradient as follows:

a intermediate material selected from the group consisting of silicon, germanium, and a combination thereof, chemically bonded to said metal alloy in said substrate forming an intermetallic material selected from the group consisting of a metal-silicide, a metal-germanide, and a combination thereof;

an interlayer comprising said intermediate material cohesively bonded to said intermetallic material;

carbon chemically bonded to said interlayer material, forming a carbide selected from the group consisting of silicon carbide, germanium carbide, and a combination thereof; and a diamond-like carbon coating cohesively bonded to said carbide.

26. The metal alloy component of claim 25 wherein said diamond-like carbon coating has a thickness of at least about 1 μ.

27. The metal alloy component of claim 25 further comprising nitrogen bonded to carbon atoms in said diamond-like carbon coating.

28. The metal alloy component of claim 26 further comprising nitrogen bonded to carbon atoms in said diamond-like carbon coating.

29. A solid metal alloy component coated with diamond-like carbon by a process comprising:

exposing said component to a vacuum at a pressure of about $10^{-5}$ torr or less;

heating said component to a first temperature of about 300° C. (149° F.) or, if said metal alloy is temperature sensitive, to a highest temperature acceptable for said metal alloy;

depositing onto said component an intermediate material selected from the group consisting of silicon, germanium, and a combination thereof in an amount sufficient to form an intermetallic material selected from the group consisting of a metal-silicide, a metal-germanide, and a combination thereof at an outer surface of said component cohesively bonded to an interlayer of said intermediate material;

substantially simultaneous with said depositing of said intermediate material, bombarding said intermediate material with a first energetic beam of ions at a first energy, a first ion arrival ratio, and for a first amount of time sufficient to form said intermetallic bonding layer cohesively bonded to said interlayer;

condensing a diamond-like carbon precursor onto said interlayer at a second temperature and for a second amount of time sufficient to form a film of precursor molecules on said interlayer, wherein said second temperature is sufficiently low that said diamond-like carbon precursor is not vaporized off of said substrate;

substantially simultaneous with said condensing of said diamond-like carbon precursor, bombarding said diamond-like carbon precursor with a second energetic beam of ions at a second energy, a second ion arrival ratio, and for a third amount of time sufficient to form a carbide bonding layer selected from the group consisting of silicon-carbide, germanium-carbide, and a combination thereof cohesively bonded to a coating of diamond-like carbon.

30. The component of claim 29 wherein said component comprises a metal alloy selected from the group consisting of cobalt, nickel, titanium, zirconium, chromium, molybdenum, tungsten, platinum, palladium, and combinations thereof.

31. The component of claim 29 wherein said diamond-like carbon coating has a thickness of at least about 1 μ.

32. The component of claim 30 wherein said diamond-like carbon coating has a thickness of at least about 1 μ.

33. The component of claim 29 wherein said second beam of ions comprises nitrogen ions.

34. The component of claim 30 wherein said second beam of ions comprises nitrogen ions.

35. The component of claim 31 wherein said second beam of ions comprises nitrogen ions.

36. The component of claim 32 wherein said second beam of ions comprises nitrogen ions.

* * * * *

UNITED STATES PATENT AND TRADEMARK OFFICE
CERTIFICATE OF CORRECTION

PATENT NO. : 5,725,573
DATED : Mar. 10, 1998
INVENTOR(S) : Geoffrey Dearnaley, et al It is certified that error appears in the above-identified patent and that said Letters Patent is hereby corrected as shown below:

On title page, after item [73]
The Terminal Disclaimer notice should read:
--The Term of this patent shall not extend beyond the expiration date of Pat. Nos. 5,593,719 and 5,605,714.--

Signed and Sealed this

Twenty-sixth Day of May, 1998

Attest:

BRUCE LEHMAN

*Attesting Officer*       *Commissioner of Patents and Trademarks*